(12) United States Patent
Yano et al.

(10) Patent No.: US 6,949,656 B2
(45) Date of Patent: Sep. 27, 2005

(54) CYCLIC AMINE DERIVATIVES AND USE THEREOF

(75) Inventors: Toshisada Yano, Osaka (JP); Isako Sakaguchi, Koka-gun (JP); Goro Katsuura, Koka-gun (JP); Naoki Yoshikawa, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 13 days.

(21) Appl. No.: 10/296,388

(22) PCT Filed: Aug. 2, 2001

(86) PCT No.: PCT/JP01/06673

§ 371 (c)(1),
(2), (4) Date: Nov. 25, 2002

(87) PCT Pub. No.: WO02/12191

PCT Pub. Date: Feb. 14, 2002

(65) Prior Publication Data

US 2004/0038966 A1 Feb. 26, 2004

(30) Foreign Application Priority Data

Aug. 8, 2000 (JP) ......................................... 2000-239647

(51) Int. Cl.[7] ..................... A61K 31/435; C07D 211/70; C07D 211/82
(52) U.S. Cl. ..................... 546/339; 546/340; 546/342; 546/344; 514/277
(58) Field of Search .......................... 514/277; 546/339, 546/340, 342, 344

(56) References Cited

U.S. PATENT DOCUMENTS

| | | | |
|---|---|---|---|
| 4,267,183 A | 5/1981 | Johnson et al. | |
| 4,521,428 A | 6/1985 | Nisato et al. | |
| 4,645,771 A | 2/1987 | Mills | |
| 6,433,165 B1 * | 8/2002 | Luly et al. | 540/522 |
| 6,649,623 B1 * | 11/2003 | Yano et al. | 514/277 |

FOREIGN PATENT DOCUMENTS

| | | |
|---|---|---|
| EP | 978512 | 2/2000 |
| GB | 2 045 750 | 11/1980 |
| WO | 99/48888 | 9/1999 |
| WO | 00/46194 | 8/2000 |

OTHER PUBLICATIONS

DeSantis, Jr., et al., "Synthesis of potential mescaline antagonists", Journal of Pharmaceutical Sciences, 65(10), pp. 1479–1484 (1976).

Möhrle et al., "Sodium mercury EDTA dehydrogenation of N–aliphatic–substituted 1, 2, 3, 6–tetrahydropyridine derivatives", Arch. Pharm. (Weinheim), 323(2), pp. 109–115 (1990).

Flann et al., "Iminium ion and acyliminium ion initiated cyclization reactions of vinylsilanes. Regiocontrolled synthesis of tetrahydropyridines and related heterocycles", J. Am. Chem. Soc., 109(20), pp. 6097–6107 (1987).

Takemura et al., "Synthesis and selective activity of cholinergic agents with rigid skeletons. III", Chem. Pharm. Bull., 29(10), pp. 3026–3032 (1981).

Ding et al., "A facile synthesis of 3–pyrrolines", Synthetic Communications, 20(2), pp. 227–230 (1990).

Chapman et al., Polycyclic systems related to [1]benzothieno [2,3–c]pyridine, J. Chem. Soc. (C), (16), pp. 2269–2272 (1970).

* cited by examiner

Primary Examiner—D. Margaret Seaman
(74) Attorney, Agent, or Firm—Wenderoth, Lind & Ponack, L.L.P.

(57) ABSTRACT

A composition for use as an antiobestic agent and preventive or therapeutic agent for diabetes, containing a compound of the formula (I):

$$A{-}(CH_2)_m{-}X{-}(CH_2)_n{-}N{-}(CH_2)_p \quad (I)$$

wherein, A is substituted aryl or substituted heteroaryl with one or more group(s); (here, one of following groups is at least contained as the substituent: $-R^A-R^B$ ($R^A$ is S, SO, $SO_2$, $NR^C$, $NR^C SO_2$ ($R^C$ is hydrogen or lower alkyl) or lower alkylene); $R^B$ is optionally substituted aryl);

X is O, S, NR wherein R is hydrogen or lower alkyl, or single bond;

m is an integer of 0 to 4;

n is an integer of 1 to 6;

p is an integer of 1 to 3, pharmaceutically acceptable salt, prodrug or hydrate thereof.

11 Claims, No Drawings

CYCLIC AMINE DERIVATIVES AND USE THEREOF

TECHNICAL FIELD

The present invention relates to cyclic amine derivatives and use thereof. These derivatives are for use as pharmaceutical compositions such as an antiobestic agent and a preventive or therapeutic agent for diabetes.

BACKGROUND ART

Nowadays, while dietary life is rich and living environment becomes convenient, the patients of obesity keep on increasing. Along with the increase thereof, other various circulatory system diseases such as diabetes, hypertension and hyperlipemia are also spreading as life habit diseases. As the basic therapy for obesity, the diet therapy and the functional therapy have been adopted. When their therapy are not so effective or the patients are of excessive obesity type, the medical therapy, administering a feeding deterrent agent such as 5-HT antagonist, has been conducted. However, the feeding deterrent agent can not essentially improve the obese physical constitution because it does not decompose lipid in obese cells. Moreover, when the feeding deterrent agent is administered to patients so as to excessively repress the appetite of patients, the amount of nutrition-intake in the daily life decreases to less than the minimum level to lead the health control problem. Further, since the feeding deterrent agent acts on the central nervous system, side effects to brain are concerned. Therefore, the feeding deterrent agent is usually used as a supplement in the basic therapy.

Further, diabetes mellitus is usually classified into two types: insulin-dependence (type I, IDDM) accompanied with the decrease of insulin-producing cells and non insulin-dependence (type II, NIDDM) which is considered to be generated by the decrease of insulin sensibility. As the clinical situation, 90% or more of the diabetes mellitus patients are involved in the latter. In the non insulin-dependence diabetes mellitus (type II diabetes mellitus), while the concentration of insulin in blood is high, the sensibility of somatic cells to insulin is decreased due to insulin-resistance. Thus, the intake of glucose existing in blood into somatic cells is inhibited. As the therapeutic agent for type II diabetes mellitus which can improve the insulin resistance, thiazolidine derivatives and the like are under development.

In J. Pharm. Pharmacol. 1962, 14, 16, some tetrahydropyridine derivatives are described as possessing an antihypertensive effect without disclosing any other use. Furthermore, some tetrahydropyridine derivatives are described in U.S. Pat. No. 4,645,771, but an inhibitory activity to platelet aggregation is described for use.

DISCLOSURE OF INVENTION

Therefore, it has been desired to develop a novel antiobestic agent. Further needed is a novel preventive or therapeutic agent for diabetes mellitus, especially type II diabetes mellitus, which is one of the diseases associated with obesity.

The present inventors have intensively studied to find out that cyclic amine derivatives have various pharmacological effects such as reducing body weight and/or lowering the concentration of insulin and glucose in blood and so they are for use as a preventive or therapeutic agent for obesity and/or diabetes and the like, whereby accomplishing the present invention shown below.

1. A composition for use as an antiobestic agent, containing a compound of the formula (I):

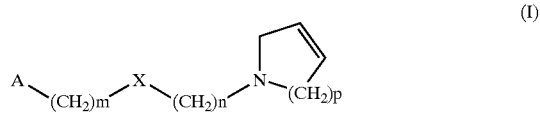

wherein A is aryl or heteroaryl, each substituted with one or more substituent(s), (wherein the substituent includes at least a group of —$R^A$—$R^B$ ($R^A$ is S, SO, $SO_2$, $NR^C$, $NR^C SO_2$ ($R^C$ is hydrogen or lower alkyl) or lower alkylene; $R^B$ is optionally substituted aryl);

X is O, S, NR (R is hydrogen or lower alkyl), or a bond;
m is an integer of 0 to 4;
n is an integer of 1 to 6;
p is an integer of 1 to 3,
pharmaceutically acceptable salt, prodrug or solvate thereof.

2. The composition for use as an antiobestic agent described in above 1 wherein X is O.

3. The composition for use as an antiobestic agent described in above 1 wherein m is 0.

4. The composition for use as an antiobestic agent described in above 1 wherein n is 2 to 4.

5. The composition for use as an antiobestic agent described in above 1 wherein p is 2.

6. The composition for use as an antiobestic agent described in above 1 wherein X is O; m is 0; n is 2 to 4; and p is 2.

7. The composition for use as an antiobestic agent described in above 1 wherein A is phenyl substituted with —$R^A$—$R^B$ ($R^A$ and $R^B$ are the same meaning as described above).

8. The composition for use as an antiobestic agent described in above 7 wherein $R^B$ is phenyl or pyridinyl, each substituted with same or different, one to three group(s) selected from the group consisting of halogen, hydroxy, lower alkyl, halogenated lower alkyl, lower alkoxy, halogenated lower alkoxy and phenyl.

9. The composition for use as an antiobestic agent described in above 1 wherein X is O; m is 0; n is 2 to 4; p is 2; and A is phenyl substituted with —$R^A$—$R^B$ ($R^A$ is the same meaning as described above; $R^B$ is substituted phenyl or substituted pyridinyl).

10. The composition for use as an antiobestic agent described in above 9 wherein $R^B$ is phenyl or pyridinyl, each substituted with halogen, halogenated lower alkyl or halogenated lower alkoxy.

11. A composition for use as a preventive or therapeutic agent for diabetes containing a compound described in any one of above 1 to 10.

12. A compound of the formula (II):

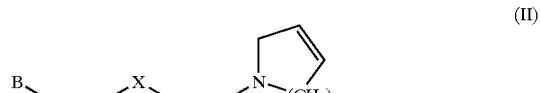

wherein B is

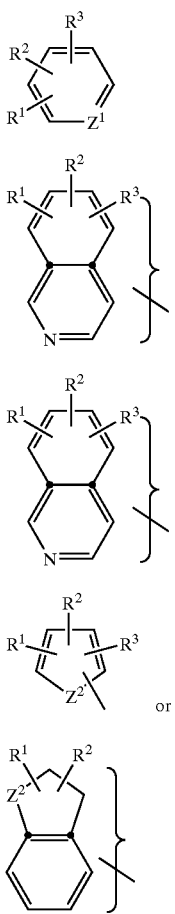

wherein R¹, R² and R³ are each independently hydrogen, halogen, hydroxy, lower alkyl, halogenated lower alkyl, piperidyl (lower) alkyl, lower alkoxy, halogenated lower alkoxy, carboxy lower alkoxy, optionally substituted aryl, —$R^A$—$R^B$ ($R^A$ is S, SO, $SO_2$, $NR^C$, $NR^C SO_2$ ($R^C$ is hydrogen or lower alkyl) or lower alkylene; $R^B$ is optionally substituted aryl), or optionally substituted aryl (lower) alkoxy; provided that at least one of R¹, R² and R³ is —$R^A$—$R^B$; $Z^1$ is CH or N; $Z^2$ is O or S;
X is O or S;
m is an integer of 0 to 4;
n is an integer of 1 to 6;
p is an integer of 1 to 3, phamaceutically acceptable salt, prodrug, or hydrate thereof.
13. The compound described in above 12 wherein X is O.
14. The compound described in above 12 wherein m is 0.
15. The compound described in above 12 wherein n is 2 to 4.
16. The compound described in above 12 wherein p is 2.
17. The compound described in above 12 wherein X is O; m is 0; n is 2 to 4 and p is 2.
18. The compound described in above 12 wherein B is a group represented by (a); $Z^1$ is CH; R¹ is —$R^A$—$R^B$ ($R^A$ and $R^B$ are the same meaning as described above); R² and R³ are both hydrogen.
19. The compound described in above 18 wherein $R^B$ is phenyl or pyridinyl, each substituted with same or different, one to three group(s) selected from the group consisting of halogen, hydroxy, lower alkyl, halogenated lower alkyl, lower alkoxy, halogenated lower alkoxy and phenyl.
20. The compound described in above 12 wherein X is O; m is 0; n is 2 to 4; p is 2; B is a group represented by (a); $Z^1$ is CH or N; R¹ is —$R^A$—$R^B$ ($R^A$ is the same meaning as described above; $R^B$ is substituted phenyl or substituted pyridinyl); and R² and R³ are both hydrogen.
21. The compound described in above 20, wherein $R^B$ is phenyl or pyridinyl, each substituted with halogen, halogenated lower alkyl or halogenated lower alkoxy.
22. A pharmaceutical composition containing a compound described in any one of above 12 to 21.
23. A composition for use as an antiobestic agent containing a compound described in any one of above 12 to 21.
24. A composition for use as a preventive or therapeutic agent for diabetes containing a compound described in any one of above 12 to 21.
25. A compound of the formula (VII):

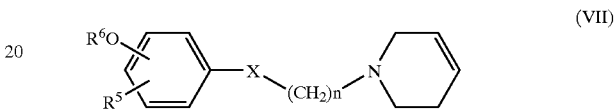

wherein X is O or $SO_2$; n is an integer of 1 to 6; $R^5$ is hydrogen or halogen; $R^6$ is optionally substituted phenyl or optionally substituted pyridinyl (wherein each substituent is halogen, halogenated lower alkyl or halogenated lower alkoxy); excluding a compound wherein X is O; n is 3; $R^5$ is hydrogen and $R^6$ is trifluoromethyl phenyl,
phamaceutically acceptable salt, prodrug, or hydrate thereof.
26. The compound described in above 25, which has any one of formulas shown below.

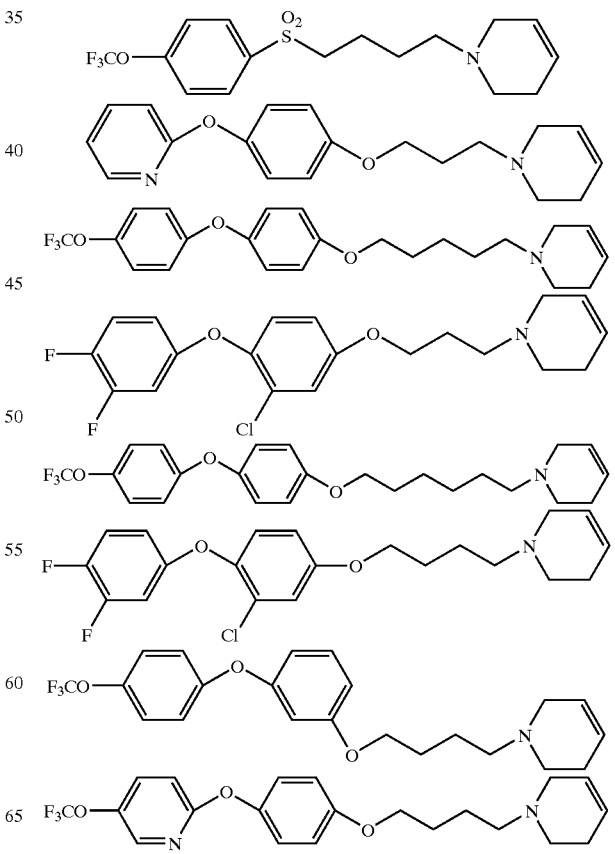

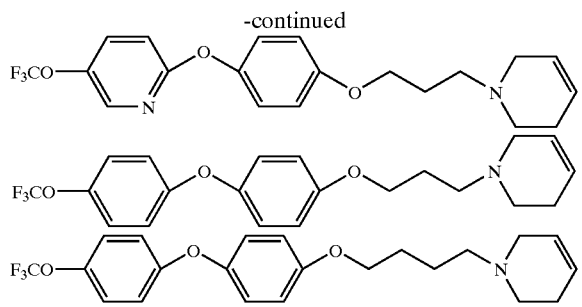

27. A pharmaceutical composition containing a compound described in any one of above 25 to 26.
28. A composition for use as an antiobestic agent containing a compound described in any one of above 25 to 26.
29. A composition for use as a preventive or therapeutic agent for diabetes containing a compound described in any one of above 25 to 26.
30. A method for preventing or treating obese or diabetes, which comprises administering a compound described in any one of above 12 to 21 or 25 to 26.
31. Use of a compound described in any one of above 12 to 21 or 25 to 26 for production of a preventive or therapeutic agent for obesity or diabetes.

BEST MODE FOR CARRYING OUT THE INVENTION

One of the structural features of compound (I) is to have an unsaturated 5- to 7-membered, preferably 6-membered cyclic amine. A more special feature is that substituted aryl or substituted heteroaryl shown by A has at least a group of —$R^A$—$R^B$ ($R^A$ and $R^B$ have the same meaning as above) as a substituent. An especially preferable compound is compound (II) within compounds (I).

One of the structural features of compound (VII) is to have optionally substituted phenyloxy or optionally substituted pyridinyloxy on the benzene ring, which is shown by —$OR^6$.

Terms used herein are explained below. Unless otherwise mentioned, each term, by itself or as part of another, has the following meaning.

Examples of lower alkyl include a straight or branched $C_1$ to $C_6$ alkyl such as methyl, ethyl, n-propyl, i-propyl, n-butyl, i-butyl, sec-butyl, t-butyl, n-pentyl, i-pentyl, neo-pentyl, tert-pentyl, n-hexyl, and the like and preferred is $C_1$ to $C_4$ alkyl, more preferred is methyl, ethyl or t-butyl.

Lower alkylene includes a straight or branched $C_1$ to $C_6$ alkylene such as methylene, ethylene, n-propylene, n-butylene, i-butylene, n-pentylene, n-hexylene and the like and preferred is $C_1$ to $C_4$ alkylene, more preferred is methylene or ethylene.

Lower alkoxy includes oxy connected with the above lower alkyl, such as methoxy, ethoxy, i-propoxy, tert-butoxy, pentyloxy, hexyloxy and the like, preferably $C_1$ to $C_4$ alkoxy, more preferably methoxy.

Halogen means F, Cl, Br and I.

Halogenated lower alkyl is preferably trihalogenated $C_1$ to $C_4$ lower alkyl, more preferably trihalogenated methyl (e.g., —$CF_3$) and the like.

Halogenated lower alkoxy is preferably trihalogenated $C_1$ to $C_4$ lower alkoxy, more preferably trihalogenated methoxy (e.g., —$OCF_3$) and the like.

Aryl means a monocyclic or fused aromatic hydrocarbon group such as phenyl, α-naphthyl, β-naphthyl, anthoryl, indenyl, phenantryl and the like and preferred is phenyl.

Heteroaryl means an aromatic monocyclic or polycyclic group containing the same or different hetero atom selected from O, S and N.

The monocyclic group includes a 5- to 6-memberd cyclic group containing one to four hetero atom, such as pyridyl, furyl, thienyl, tetrazolyl, pyrolyl, pyrazolyl, imidazolyl, oxazolyl, thiazolyl, thiaziazolyl, oxazinyl, triazinyl and the like and preferably pyridinyl (e.g., 2-pyridinyl), furyl (e.g.,: 2-furyl) or thienyl (e.g., 2-thienyl).

The polycyclic group includes a 2- or 3-cyclic hetero cyclic group containing one to five hetero atom and preferred is a 8- to 14-membered cyclic group such as quinolyl, isoquinolyl, indoryl, benzoimidazolyl, indazolyl, indorydinyl, benzofuryl, benzothienyl, acrydinyl, phenanthrydinyl and the like, and preferably quinolyl (e.g., 4-quinolyl), isoquinolyl (e.g., 5-isoquinolyl), benzothienyl (e.g., 5-benzothienyl), benzofuryl (e.g., 5-benzofuryl).

When the above aryl or heteroaryl is substituted, examples of the substituent include a same or different group selected from the group consisting of halogen, lower alkyl, lower alkoxy, lower alkylthio, hydroxy, amino, carboxy, cyano, nitro, lower alkylcarbonyl, lower alkoxycarbonyl, halogenated lower alkyl, halogenated lower alkoxy, pyperidyl (lower) alkyl, carboxy (lower) alkoxy, optionally substituted aryl, optionally substituted aryloxy, optionally substituted aryl (lower) alkoxy, —$R^A$—$R^B$ ($R^A$ is S, SO, $SO_2$, $NR^C$, $NR^CSO_2$ ($R^C$ is hydrogen or lower alkyl), or lower alkylene; $R^B$ is optionally substituted aryl) and the like. These may be located at any substitutable position in a range of one to five, preferably one to three.

Futhermore, as each substituent of the optionally substituted aryl, the optionally substituted aryloxy and the optionally substituted aryl (lower) alkoxy, exemplified are same or different one to three group(s) selected from the group consisting of halogen, hydroxy, lower alkyl (such as methyl, t-butyl), halogenated lower alkyl (such as —$CF_3$), lower alkoxy (such as —$OCH_3$), halogenated lower alkoxy (such as —$OCF_3$), phenyl and the like. These may be located at any substitutable position.

A is preferably the group exemplified by (a) to (e) in the above B, preferably substituted phenyl shown by (a) ($Z^1$= CH); more preferably $R^1$ is —$R^A$—$R^B$ ($R^A$ and $R^B$ are the same meaning as above): $R^2$ and $R^3$ are both hydrogen. The substitutent of $R^1$ is preferably p-position. $R^A$ is preferably S, $SO_2$ or $CH_2$. $R^B$ is preferably substituted phenyl or substituted pyridinyl. The substituent is same or different, one to three group selected from the group consisting of halogen (such as F, Cl, Br. Di-F, tri-F), hydroxy, lower alkyl (such as $CH_3$, t-Bu), halogenated lower alkyl (such as —$CF_3$), lower alkoxy (such as —$OCH_3$), halogenated lower alkoxy (such as —$OCF_3$) and Phenyl. More preferable substituent is halogen, halogenated lower alkyl or halogenated lower alkoxy. $R^B$ is more preferably phenyl or pyridinyl, each substituted with F, Br, p-trifluoromethyl, and/or p-trifluoromethoxy and the like.

X is preferably O or S, more preferably O.

m is preferably 0.

n is preferably 2 to 4, more preferably 3 or 4.

p is preferably 2.

As compound (II), preferable is a case, wherein X is O; m is 0; n is 2 to 4; p is 2; B is a group shown by (a); $Z^1$ is CH; $R^1$ is —$R^A$—$R^B$ ($R^A$ is the same meaning as above; $R^B$ is substituted phenyl); and $R^2$ and $R^3$ are both hydrogen, more preferably, $R^B$ is phenyl or pyridinyl each substituted preferably at the p-position with halogen, halogenated lower alkyl, or halogenated lower alkoxy.

In compound (VII), preferably X is O; n is 2 to 4; $R^5$ is hydrogen; $R^6$ is optionally substituted phenyl or optionally substituted pyridinyl (substituent: —$CF_3$, —$OCF_3$ and the like) and/or —$OR_6$ is the para-position. Furthermore, preferably the substituent on phenyl or pyridinyl is one or two of halogen (such as F, Cl) and $R^5$ is halogen (F). More preferable compound is the one described in the later Example 17 to 27.

The preparation of the compound(I) is exemplified below and the compound (II) and compound (VII) can be prepared likewise. Compound (VII) can also be prepared by the procedure cited in WO 00/46194.

Preparation 1

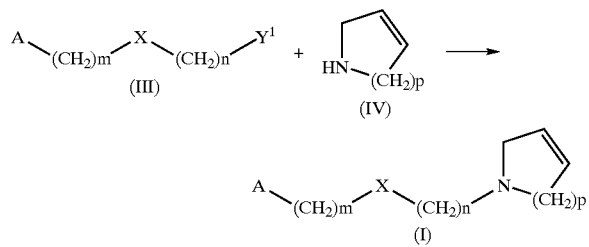

wherein, $Y^1$ is a leaving group such as halogen, the other symbols are the same meaning as described above.

The compound (III) and the compound (IV) are reacted, if necessary in the presence of a base, to give the compound (I). As the base, carbonate (e.g., $K_2CO_3$, $Na_2CO_3$ and the like), NaOH, tertiary amine and the like can be used. Furthermore, KI may be used together with them. As a solvent, $CH_3CN$, dimethylformamide (DMF), dimethylsulfoxide (DMSO), methylethylketone (MEK) and the like can be used. The reaction temperature is usually about 10 to 200° C., preferably room temperature to about 110° C., and reaction time is several hours to several ten hours, preferably about one to 20 hours, more preferably about 3 to 15 hours. The compound (III) and the compound (IV) are prepared by known reactions or may be commercially available products.

Preparation 2

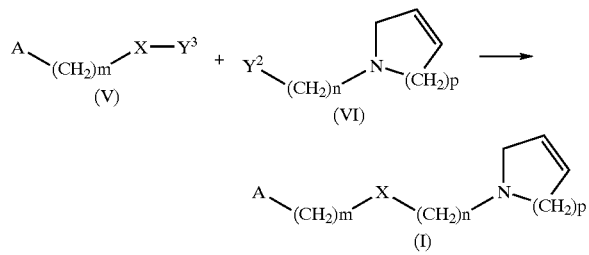

wherein $Y^2$ is halogen or the like, $Y^3$ is hydrogen in the case of X=O, S or a leaving group (e.g., halogen, —$COCF_3$ and the like), in the case of X=NR, the other symbols are the same meaning as described above.

The compound (V) and the compound (VI) are reacted, if necessary in the presence of a base, to give the compound (I). As the base, carbonate (e.g., $K_2CO_3$, $Na_2CO_3$ and the like), NaOH, tertiary amine and the like can be used. Moreover, KI may be used together with them. As a solvent, $CH_3CN$, dimethylformamide (DMF), dimethylsulfoxide (DMSO), methylethylketone (MEK) and the like can be used. The reaction temperature is usually about 10 to 200° C., preferably room temperature to about 110° C. The reaction time is several hours to several ten hours, preferably about 1 to 20 hours, more preferably about 3 to 15 hours. The compound (V) and the compound (VI) are prepared by known reactions or may be commercially available products.

Prior to the above each reaction, a functional group may be protected by a method well known to skilled persons and if necessary deprotected after the reaction.

Examples of the pharmaceutically acceptable salt of the present compound include salts formed with inorganic bases, ammonia, organic bases, inorganic acids, organic acids, basic amino acids, halogen ions or the like, and inner molecular salts. Examples of the inorganic base include alkaline metal (e.g., Na, K) and alkaline earth metal (e.g., Ca, Mg). Examples of the organic base include trimethylamine, triethylamine, choline, procaine, ethanolamine and the like. Examples of the inorganic acid include hydrochloric acid, hydrobromic acid, sulfuric acid, nitric acid, and phosphoric acid and the like. Examples of the organic acid include p-toluene sulfonic acid, methanesulfonic acid, formic acid, trifluoroacetic acid and maleic acid and the like. Examples of the basic amino acid include lysine, arginine, ornithine, histidine and the like. The compound may be hydrate.

Prodrug means a derivative of the present invention compound, which has a chemically or metabolically decomposable group and is converted, by solvolysis or under physiological conditions, to a compound of present invention which is pharmaceutically active in vivo. A preparation of an appropriate prodrug-derivative is described in, e.g., Design of Pro agents Elsevier, Amsterdam 1985. When the compound of present invention has a carboxy group, examples of the prodrug include an ester derivative prepared by reacting a proper alcohol with an original acidic compound or an amide derivative prepared by reacting a proper amine with an original acidic compound. When the compound of present invention has a hydroxyl group, examples of the prodrug include an acyloxy derivative prepared by reacting a proper acylhalide or a proper acidic anhydrate with a hydroxyl group-containing compound. When the compound of present invention has an amino group, examples of prodrug include an amide derivative prepared by reacting a proper acidic haloganated compound or a proper mixed acidic anhydrate with an amino group-containing compound.

The present compound can be administered orally or parenterally to animal including man as a pharmaceutical composition, especially antiobestic agent or preventive or therapeutic agent for diabetes. Examples of the administered form include granules, tablets, capsules, injections and the like. In formulation, various additives can be used such as excipients, disingrators, binders, lubricants, stabilizers, coloring agents, coating agents if necessary. Although the dosage of the compound of the present invention may vary depending on the age, weight, conditions of the patient, and the administration route and the like, the daily dose for adult can generally be about 20 to 1000 mg for oral administration. For parenteral administration, the daily dose can be about 2 to 10 mg.

A more preferable compound of the present invention is for use as a medicament, since the compound dose not repress the appetite excessively, has a well oral absorbability, shows a high concentration in blood, has weak inhibitory effects on metabolic enzymes and/or dose not show any side effect on the central nervous systems, digestive organs and the like.

Abbreviation

Me=methyl, t-Bu=t-butyl, Ph=phenyl, Bn=benzyl, Pd$_2$(dba)$_3$=tris(benzylideneacetone)dipalladium(0), MCPBA=m-chloroper benzoic acid, Hexane=hexane, AcOEt=EtOAc, DMF=dimethylformamide, MeOH=methanol, EtOH=ethanol, DMSO=dimethylsulfoxide, Bu$_4$NBr=tetrahbutylammonium bromide, Ex means No. of experimental.

EXAMPLE 1 OF REFERENCE

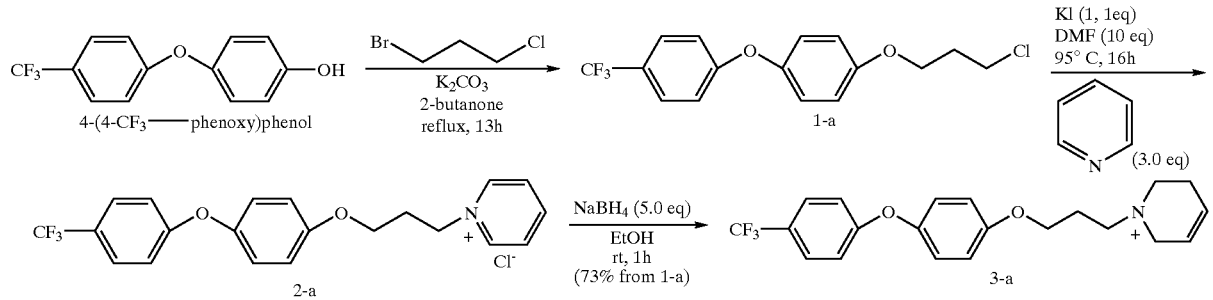

(1) Compound 2-a

KI 5.63 g was added to a solution of compound 1-a (10.2 g) and pyridine 7.48 ml in DMF 102 ml. The mixture was stirred for 23 h at 95° C. and concentrated under a reduced pressure. The residue was extracted with chloroform and concentrated under a reduced pressure to give an oil 2-a.

NMR(CDCl$_3$)δ ppm (300 MHz) 2.658 (2H, quint, J=6.0 Hz), 4.180(2H, t, J=5.7 Hz), 5.297(2H, t, J=6.3 Hz), 6.792 (2H, d, J=9 Hz), 6.94~7.00(4H, m), 7.545(2H, d, J=8.4 Hz), 8.111(2H, dd, J=7.8 Hz, 6.9 Hz), 8.523(1H, t, J=7.8 Hz), 9.447(2H, d, J=6.9 Hz)

(2) Compound 3-a

The crude product 2-a was dissolved in EtOH 204 ml. NaBH$_4$ 5.83 g was added in small portions with cooling in ice. The mixture was stirred for 1 h with cooling in ice and for 1 h at room temperature and was concentrated under a reduced pressure. Chloroform and ice-water were added to the residue. The aqueous phase was extracted with chloroform. The combined organic phases were washed with brine, dried over anhydrous MgSO$_4$ and concentrated under a reduced pressure. The residue was chromatographed on silica gel (AcOEt/EtOH, 20/1) to give colorless oil, 3-a.

Anal. (%): C$_{21}$H$_{22}$F$_3$NO$_2$.HCl

Calcd.: C=60.95,H=5.60,N=3.38,Cl=8.57,F=13.77.

Found: C=60.86,H=5.50,N=3.45,Cl=8.55,F=13.68.

NMR (CDCl$_3$)δ ppm (300 MHz)(Free) 2.031(2H, quint, J=6.3 Hz) 2.14~2.27(2H, m) 2.55~2.65(4H, m) 2.97~3.04 (2H, m)4.034(2H, t, J=6.3 Hz) 5.65~5.83(2H, m) 6.90~7.04 (6H, m) 7.534(2H, d, J=9 Hz).

EXAMPLE 1

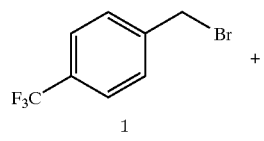

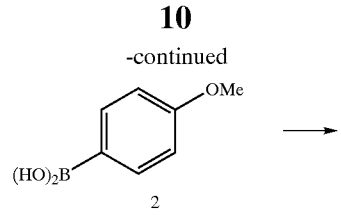

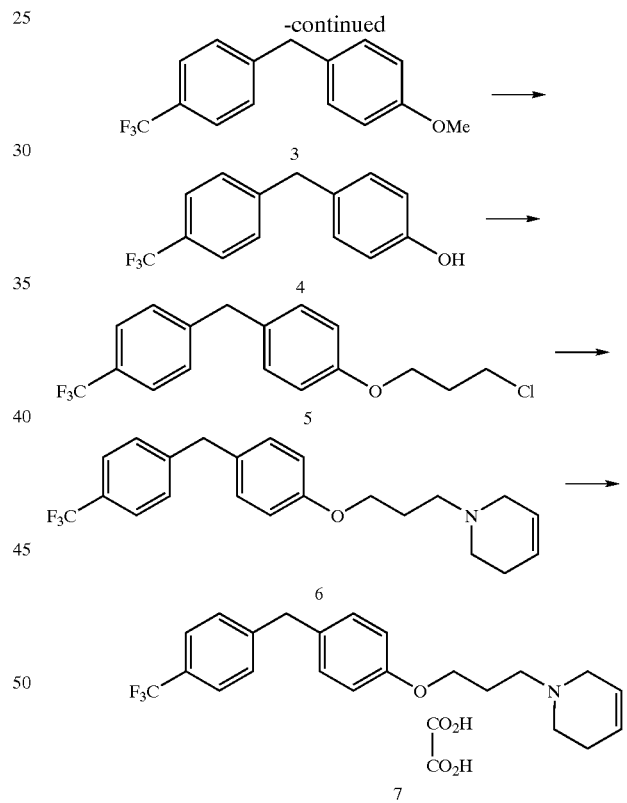

(1) Compound 3

Compound 1 (10.24 g, 42.84 mmol), compound 2 (4-methoxyphenylboric acid 9.11 g, 59.98 mmol), Pd(PPh$_3$)$_4$ (990 mg, 0.86 mmol) and 2 M Na$_2$CO$_3$ (60 mL) in dimethoxyethane (150 mL) were heated under reflux for 0.5 h. Water was added. The mixture was extracted with ether. The organic phases were washed with 1N NaOH, water and brine, dried over MgSO$_4$ and concentrated under a reduced pressure. The residue was chromatographed on silica gel (toluene/hexane, 9/1) to give colorless oil 3 (11.41 g, 100%).

C$_{15}$H$_{13}$F$_3$O

NMR (CDCl$_3$)δ ppm (300 MHz) 3.79(3H, s), 3.97(2H, s), 6.85(2H, d, J=8.7 Hz), 7.09(2H, d, J=8.7 Hz), 7.28(2H, d, J=8.0 Hz), 7.53(2H, d, J=8.0 Hz)

(2) Compound 4

Compound 3 (11.41 g, 42.84 mmol) and pyridine HCl salt (34.65 g, 299.9 mmol) were stirred for 0.5 h at 210° C. and cooled to the room temperature. Water was added. The mixture was extracted with ether. The organic phases were washed with water and brine, dried over anhydrous MgSO$_4$ and concentrated under a reduced pressure. The residue was chromatographed on silica gel (AcOEt/hexane, 1/4) to give a colorless oil 4 (10.39 g, 95%).

$C_{14}H_{11}F_3O$

NMR (CDCl$_3$)δ ppm (300 MHz) 3.96(2H, s), 4.75(1H, br), 6.77(2H, d, J=8.6 Hz), 7.04(2H, d, J=8.6 Hz), 7.27(2H, d, J=8.0 Hz), 7.53(2H, d, J=8.0 Hz)

(3) Compound 5

Compound 4 (2.00 g, 7.93 mmol), 3-bromo-1-chloropropane (1.50 g, 9.51 mmol) and K$_2$CO$_3$ (1.64 g, 11.9 mmol) in 2-butanone (40 mL) were heated under reflux for 6 h. The precipitate was filtered off and the mother liquor was concentrated under a reduced pressure. The residue was chromatographed on silica gel (AcOEt/hexane, 1/5) to give colorless crystals of 5 (2.26 g, 86%).

$C_{17}H_{16}OClF_3$

NMR (CDCl$_3$)δ ppm (300 MHz) 2.18–2.26(2H, m), 3.74 (2H, t, J=6.3 Hz), 3.97(2H, s), 4.09(2H, t, J=5.7 Hz), 6.84(2H, d, J=8.7 Hz), 7.08(2H, d, J=8.7), 7.28(2H, d, J=8.1 Hz), 7.57(2H, d, J=8.1)

(4) Compound 6

Compound 5 (2.00 g, 6.08 mmol), 1,2,3,6-tertrahydropyridine (556 mg, 6.69 mmol), potassium carbonate (1.26 g, 9.12 mmol) and KI (1.11 g, 6.69 mmol) in DMF (40 mL) were heated at 80° C. for 3 h and concentrated under a reduced pressure. Acetone was added and the precipitate was filtered off. The mother liquor was concentrated under a reduced pressured and the residue was chromatographed on silica gel (CHCl$_3$/MeOH, 95/5) to give a yellow oil 6 (2.03 g, 89%).

$C_{22}H_{24}NOF_3$

NMR (CDCl$_3$)δ ppm (300 MHz) 1.98~2.07(2H, m), 2.17~2.22(2H, m), 2.59~2.64(4H, m), 3.01~3.03(2H, m), 3.96~4.03(4H, m), 5.65~5.78(2H, m), 6.84(2H, d, J=8.7 Hz), 7.07(2H, d, J=8.7 Hz), 7.27(2H, d, J=8.1 Hz), 7.52(2H, d, J=8.1 Hz)

(5) Compound 7

A solution of oxalic acid (1.01 g, 7.99 mmol) in ethanol (10 mL) was added to a solution of compound 6 (3.00 g, 7.99 mmol) in EtOH (20 mL). The appeared crystals were collected by filtration and recrystallized from EtOH to give colorless crystals 7 (3.02 g, 81%).

Anal. (%): $C_{22}H_{24}NOF_3 \cdot C_2H_2O_4 \cdot 0.3$ (EtOH)

Calcd.: C=61.65, H=5.85, N=2.29, F=11.89.

Found: C=61.57, H=5.81, N=3.02, F=11.77.

m.p.: 146–149° C.

NMR (DMSO-d$_6$)δ ppm (300 MHz) 2.08~2.15(2H, m), 2.32(2H, br), 2.50~2.51(2H, m), 3.11~3.19(4H, m), 3.60 (2H, br), 3.98(2H, s), 4.01(2H, t, J=6.0 Hz), 5.68~5.71(1H, m), 5.86~5.90(1H, m), 6.87(2H, d, J=8.1 Hz), 7.17(2H, d, J=8.1 Hz), 7.43(2H, d, J=8.1 Hz), 7.64(2H, d, J=8.1 Hz).

EXAMPLE 2

(1) Compound 10

A mixture of compound 8 (2.25 g, 10.0 mmol), compound 9(4-benzyloxyaniline (2.39 g, 12.0 mmol), Pd$_2$(dba)$_3$ (23 mg, 0.025 mmol), (R)-(+)-2,2'-bis(diphenylphosphino)-1,1'-binaphthyl (47 mg, 0.075 mmol) and sodium isopropoxide (1.15 g, 14.0 mmol) in toluene (20 ml) was heated under reflux for 18. Water was added. The mixture was extracted with AcOEt. The organic phases were dried over anhydrous MgSO$_4$ and concentrated under a reduced pressure. The residue was chromatographed on silica gel (AcOEt/hexane, 1/4) to give compound 10 (1.98 g, 58%).

$C_{20}H_{16}NOF_3$

NMR (DMSO-d$_6$)δ ppm (300 MHz) 5.08(2H, s), 6.95~7.13(6H, m), 7.33~7.46(7H, m), 8.42(1H, s)

(2) Compound 11

A mixture of compound 10 (1.94 g, 5.65 mmol) and 5% Pd—C (194 mg) in EtOH (20 mL) was stirred for 20 h under a hydrogen atmosphere at room temperature. The solid was filtered off and the mother liquor was concentrated under a reduced pressure and purified by chromatography on silica gel (toluene/AcOEt, 9/1) to give a brown oil 11 (1.43 g, 100%).

$C_{13}H_{10}NOF_3$

NMR (DMSO-d$_6$)δ ppm (300 MHz) 6.76(2H, d, J=8.7 Hz), 6.89(2H, d, J=8.7 Hz), 7.00(2H,d, J=8.9 Hz), 7.42(2H, d, J=8.9 Hz), 8.26(1H, s), 9.24(1H, br)

(3) Compound 12

A mixture of compound 11 (85 mg, 0.335 mmol), 3-bromo-1-chloropropane (63 mg, 0.402 mmol) and K$_2$CO$_3$ (69 mg, 0.503 mmol) in 2-butanone (2 mL) was heated under reflux for 16 h. The insoluble materials were removed by filtration and the mother liquor was concentrated under a reduced pressure. The residue was chromatographed on silica gel (EtOAc/hexane, 1/3) to give a yellow oil 12 (98 mg, 89%).

$C_{16}H_{15}NOClF_3$

NMR (DMSO-$d_6$)δ ppm (300 MHz) 2.12~2.21(2H, m), 3.80(2H, t, J=6.5 Hz), 4.07(2H, t, J=6.0), 6.93~6.97(4H, m), 7.12(2H, d, J=8.9 Hz), 7.45(2H, d, J=8.9 Hz), 8.43(1H, s)

(4) Compound 13

A mixture of compound 12 (90 mg, 0.273 mmol), 1,2,3,6-tetrahydropyridine (25 mg, 0.300 mmol), $K_2CO_3$ (57 mg, 0.410 mmol) and KI (50 mg, 0.333 mmol) in DMF (2 mL) was stirred at 80° C. for 3 h. Water was added. The mixture was extracted with ether. The organic phases were washed with water and brine, dried over anhydrous $MgSO_4$ and concentrated under a reduced pressure. The residue was chromatographed on silica gel ($CHCl_3$/MeOH, 95/5) and recrystallized from AcOEt/hexane to give colorless crystals 13 (38 mg, 37%).

$C_{21}H_{23}N_2OF_3$

Calcd.: C=67.01,H=6.16,N=7.44, F=15.14.
Found: C=66.91,H=6.18,N=7.50,F=14.90.
m.p.: 95.5–96.5° C.

NMR (DMSO-$d_6$)δ ppm (300 MHz) 1.84~1.93(2H, m), 2.07~2.09(2H, m), 2.46~2.51(4H, m), 2.88~2.90(2H, m), 3.98(2H, t, J=6.3 Hz),5.62~5.72(2H, m),6.92(2H, d, J=9.0 Hz), 6.95(2H, d J=8.6 Hz),7.10(2H, d, J=9.0 Hz),7.44(2H, d, J=8.6 Hz), 8.40(1H, s)

EXAMPLES 3~5 filtration. The filtrate was concentrated under a reduced pressure. Water was added. The mixture was extracted with $Et_2O$. The extracts were dried over anhydrous $MgSO_4$ and concentrated under a reduced pressure. The residue was treated with hexane to give compound 15, 21.78 g.

$C_{14}H_{11}F_3OS$ FW 284.30

Calcd.: C=59.15,H=3.90,F=20.05,S=11.28.
Found: C=59.06,H=3.90,F=19.96,S=11.18.
m.p.: 85–86° C.

NMR (CD $Cl_3$)δ ppm (300 MHz) 7.47(2H, d, J=8.7 Hz), 7.43(2H, d, J=9.0 Hz), 7.13(2H, d, J=9.0 Hz), 6.95(2H, d, J=8.7 Hz), 3.85(3H, s).

(2) Compound 15 (1.7 g, 6 mmol) was dissolved in $CHCl_3$ 40 ml. MCPBA 2.27 g (2.2 eq) was added at room temperature. The mixture was stirred for 1.5 h, washed with saturated aqueous $NaHCO_3$, dried over anhydrous $MgSO_4$ and concentrated under a reduced pressure. The residue was chromatographed on silica gel 100 g (hexane/AcOEt 2:1). The first part of the elution was recrystallized from AcOEt-hexane to give compound 17 1.18 g (62%).

$C_{14}H_{11}F_3O_3S$ FW 316.30

Calcd.: C=53.16,H=3.51, F=18.02,S=10.14.
Found: C=53.07,H=3.36,F=17.92,S=10.15.
m.p.: 112–113° C.

NMR ($CDCl_3$)δ ppm (300 MHz) 8.04(2H, dd, J=0.6 Hz, 9.0 Hz), 7.89(2H, d, J=9.0 Hz), 7.75(2H, dd, J=0.6 Hz, 9.0 Hz), 6.99(2H, d, J=9.0 Hz), 3.85(3H, s).

The next part of the elution was also recrystallized from AcOEt-hexane to give compound 16 657 mg(36%).

$C_{14}H_{11}F_3O_2S$ FW 300.30

Calcd.: C=55.99,H=3.69,F=18.98,S=10.68.

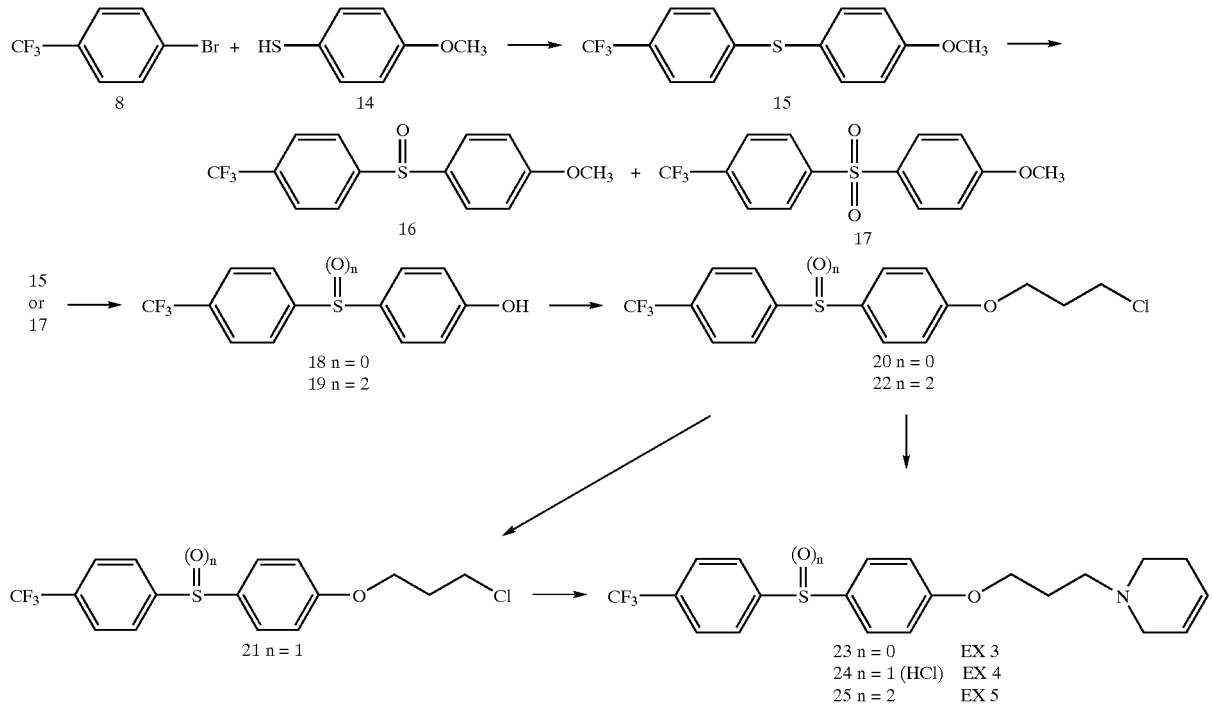

(1) NaOH 4.4 g (0.11 mol) was added to a solution of compound 8 (18.52 g, 82.3 mmol) and compound 14 (15.38 g, 0.11 mol) in anhydrous DMF 82 ml. After NaOH was dissolved, the solution was heated under reflux for 5 h. The insoluble materials were removed by Found: C=55.85, H=3.46,F;=18.92,S=10.71.
m.p.: 94–95° C.
Mass analysis: m/z 301[M+H]

NMR (CDCl$_3$)δ ppm (300 MHz) 7.74(2H, d, J=9.0 Hz), 7.71(2H, d, J=9.0 Hz), 7.58(2H, d, J=9.0 Hz), 6.98(2H, d, J=9.0 Hz), 3.83(3H, s)

(3) A mixture of compound 15 (4.53 g, 16 mmol) and pyridinium chloride 13 g (7 eq) was stirred for 1 h at 210° C. of the bath temperature. Water was adde to the cooled mixture, which was extracted with AcOEt. The extracts were dried over anhydrous MgSO$_4$ and concentrated under a reduced pressure. The residue was chromatographed on silica gel 50 g (hexane-AcOEt 2:1) to give compound 18 4.35 g (100%). Furthermore, compound 18 could be obtained by treating compound 16 with pyridinium chloride.

C$_{13}$H$_9$F$_3$OS m.p.: 53–55° C.

NMR (CDCl$_3$)δ ppm (300 MHz) 7.44(2H, d, J=8.1 HZ), 7.43(2H, d, J=8.7 Hz), 7.14(2H, d, J=8.1 Hz), 6.89(2H, d, J=8.7 Hz), 5.10(1H, br)

By the similar treatment, compound 17 (6.17 g) gave compound 19 (6.1 g, solid, 100%).

NMR (CDCl$_3$)δ ppm (300 MHz) 8.03(2H, d, J=8.4 Hz), 7.84(2H, d, J=9.0 Hz), 7.75(2H, d, J=8.1 Hz), 6.94(2H, d, J=8.7 Hz), 6.0(1H, br)

(4) A mixture of compound 18 (4.3 g, 15.9 mmol), 1-bromo-3-chloropropane 3.0 g (1.2 eq) and K$_2$CO$_3$ 4.39 g (2 eq) in 2-butanone 150 ml was heated under reflux for 8 h. The inorganic materials were removed by filtration and the filtrate was concentrated under a reduced pressure. The residue was chromatographed on silica gel 100 g (hexane/AcOEt, 9:1) to give compound 20 (5.57 g, solid, 100%).

NMR (CDCl$_3$)δ ppm (300 MHz) 7.46(2H, d, J=8.7 Hz), 7.43(2H, d, J=8.1 Hz), 7.14(2H, d, J=8.1 Hz), 6.95(2H, d, J=8.7 Hz), 4.15(2H, t, J=5.8 Hz), 3.77(2H, d, J=6.3 Hz), 2.27(2H, quint, J=6.1 Hz).

(5) A mixture of compound 20 (2.35 g, 6.78 mmol), 1,2,3,6-tetrahydropyridine 563 mg (6.78 mmol), K$_2$CO$_3$ 1.4 g (1.5 eq), KI 1.12 g(1.0 eq) and Bu$_4$NBr 0.44 g (0.2 eq) in anhydrous DMF 20 ml was stirred for 5 h at 80° C. Water was added. The mixture was extracted with AcOEt. The extracts were washed with water, dried and concentrated under a reduced pressure. The residue was chromatographed on silica gel 100 g (CHCl$_3$-MeOH 19:1) to give compound 23 2.19 g (82%), (Experimental 3).

C$_{21}$H$_{22}$F$_3$NOS FW 393.47

Calcd.: C=64.10,H=5.64,F=14.48,N=3.56,S=8.15.
Found: C=64.00,H=5.61,F=14.26,N=3.59,S=7.97.

m.p.: 49–50° C.

NMR (CDCl$_3$)δ ppm (300 MHz) 7.45(2H, d, J=9.0 Hz), 7.43(2H, d, J=8.4 Hz), 7.13(2H, d, J=8.4 Hz), 6.95(2H, d, J=9.0 Hz), 5.79–5.74(1H, m), 5.70–5.66(1H, m), 4.07(2H, t, J=6.3 Hz), 3.02(2H, t, J=2.4 Hz), 2.62(2H, t, J=7.4 Hz), 2.61(2H, t, J=5.6 Hz), 2.21(2H, m), 2.06(2H, quint, J=7.2 Hz).

(6) Compound 21 (4.35 g 12.5 mmol) was dissolved in CHCl$_3$ 150 ml. MCPBA 2.6 g (1.2 eq) was added. The solution was stirred for 1 h at room temperature, washed with aqueous saturated NaHCO$_3$, dried over anhydrous MgSO$_4$ and concentrated under a reduced pressure. The residue was chromatographed on silica gel 150 g (hexane/AcOEt, 2/1) to give compound 21 (4.03 g, oil, 88%).

NMR (CDCl$_3$)δ ppm (300 MHz) 7.74(2H, d, J=9.0 Hz), 7.71(2H, d, J=9.0), 7.58(2H, d, J=9.0 Hz), 6.98(2H, d, J=9.0 Hz), 4.14(2H, t, J=5.7 Hz), 3.72(2H, t, J=6.2 Hz), 2.23(2H, quint, J=6.0 Hz).

(7) A mixture of compound 21 (2.335 g, 6.4 mmol), 1,2,3,6-tetrrahydropyridine 535 mg (6.4 mmol), K$_2$CO$_3$ 1.33 g (1.5 eq), KI 1.07 g (1.0 eq) and Bu$_4$NBr 415 mg (0.2 eq) in anhydrous DMF 20 ml was stirred for 5 h at 80° C. Water was added.

The mixture was extracted with AcOEt. The extracts were washed with water, dried and concentrated under a reduced pressure. The residue was chromatographed on silica gel 100 g (CHCl$_3$/MeOH, 9/1) to give compound 24 (2.48 g, 90%). The compound was converted to the HCl salt, crystallized and recrystallized from i-PrOH-hexane (Experimental 4).

C$_{21}$H$_{22}$F$_3$NO$_2$S.HCl.0.6H$_2$O FW 456.74

Calcd.: C=55.22,H=5.34,Cl=7.76,F=12.48,N=3.07,S= 7.02.
Found: C=55.26,H=5.26,Cl=8.04,F=12.25,N=3.28,S= 6.94.

m.p.: 155–157° C.

NMR (CDCl$_3$)δ ppm (300 MHz) 12.80(1H, br),7.74(2H, d, J=9.0 Hz),7.72(2H, d, J=9.0 Hz), 7.59(2H, d, J=9.0 Hz), 6.96(2H, d, J=9.0 Hz), 6.03(1H, d, J=9.6 Hz), 5.71(1H, d, J=9.6 Hz), 4.15(2H, t, J=5.8 Hz), 4.00(1H, d, J=15.3 Hz), 3.55–3.51(1H, m), 3.37(1H, d, J=15.3 Hz), 3.26(2H, t, J=5.7 Hz), 3.11~3.01(1H, m), 2.95~2.84(1H, m), 2.59~2.46(2H, m), 2.39~2.31(1H, m).

(8) A mixture of compound 19 (6.1 g, 20 mmol), 1-bromo-3-chloropropane 3.8 g (1.2 eq) and K$_2$CO$_3$ 5.53 g (2 eq) in 2-butanone was heated under reflux for 7 h. The inorganic materials were removed by filtration and concentrated under a reduced pressure. The residue was chromatographed on silica gel 150 g (CHCl$_3$/acetone, 9/1) to give compound 22 (7.65 g, solid, 100%).

NMR (CDCl$_3$)δ ppm (300 MHz) 8.04(2H, d, J=8.7 Hz), 7.89(2H, d, J=8.7 Hz), 7.75(2H, d, J=9.0 Hz), 7.00(2H, d, J=8.7 Hz), 4.17 (2H, t, J=6.0 Hz), 3.73(2H, t, J=6.1 Hz), 2.25(2H, quint, J=6.0 Hz).

(9) A mixture of compound 22 (2.47 g, 6.5 mmol), 1,2,3,6-tetrahydropyridine 542 mg (6.5 mmol), K$_2$CO$_3$ 1.35 g (1.5 eq), KI 1.08 g (1 eq) and Bu$_4$NBr 0.42 g (0.2 eq) in anhydrous DMF 20 ml was stirred for 5 h at 80° C. Water was added. The mixture was extracted with AcOEt. The extracts were washed with water, dried and concentrated under a reduced pressure. The residue was chromatographed on silica gel 100 g (CHCl$_3$/MeOH, 19:1) and recrystallized from hexane to give compound 25 (1.97 g, 71%) (Experimental 5).

C$_{21}$H$_{22}$F$_3$NO$_3$S FW 425.47

Calcd.: C=59.28,H=5.21,F=13.39,N=3.29,S=7.54.
Found: C=59.12,H=5.26,F=13.05,N=3.37,S=7.49.

m.p.: 75–77° C.

NMR (CDCl$_3$)δ ppm (300 MHz) 8.03(2H, d, J=8.4 Hz), 7.87(2H, d, J=9.0 Hz), 7.75(2H, d, J=8.1 Hz),6.99(2H, d, J=9.0 Hz), 5.78–5.73(1H, m), 5.69–5.64(1H, m), 4.08(2H, t, J=6.3 Hz),2.99(2H, t, J=2.6 Hz), 2.57(2H, t, J=6.4 Hz), 2.56(2H, t, J=6.4 Hz), 2.18(2H, m), 2.03(2H, quint, J=7.0 Hz).

EXAMPLE 6

Structures of other compounds were shown below.

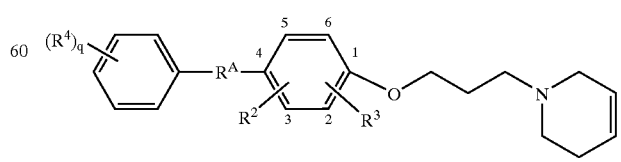

q = integer of 1 to 3

TABLE 1

R^A = CH_2

| 化合物(II-a) No | R2 | R3 | (R4)q |
|---|---|---|---|
| 1 | 3-Cl | H | F |
| 2 | 3-Br | H | F |
| 3 | 2-F | 3-F | F |
| 4 | 2-tBu | 5-tBu | F |
| 5 | 3-CF$_3$ | H | F |
| 6 | 3-Cl | H | Cl |
| 7 | 3-Br | H | Cl |
| 8 | 2-F | 3-F | Cl |
| 9 | 2-tBu | 5-tBu | Cl |
| 10 | 3-CF$_3$ | H | Cl |
| 11 | 3-Cl | H | Br |
| 12 | 3-Br | H | Br |
| 13 | 2-F | 3-F | Br |
| 14 | 2-tBu | 5-tBu | Br |
| 15 | 3-CF$_3$ | H | Br |
| 16 | 3-Cl | H | OCF$_3$ |
| 17 | 3-Br | H | OCF$_3$ |
| 18 | 2-F | 3-F | OCF$_3$ |
| 19 | 2-tBu | 5-tBu | OCF$_3$ |
| 20 | 3-CF$_3$ | H | OCF$_3$ |
| 21 | 3-Cl | H | OMe |
| 22 | 3-Br | H | OMe |
| 23 | 2-F | 3-F | OMe |
| 24 | 2-tBu | 5-tBu | OMe |
| 25 | 3-CF$_3$ | H | OMe |
| 26 | 3-Cl | H | Me |
| 27 | 3-Br | H | Me |
| 28 | 2-F | 3-F | Me |
| 29 | 2-tBu | 5-tBu | Me |
| 30 | 3-CF$_3$ | H | Me |
| 31 | 3-Cl | H | t-Bu |
| 32 | 3-Br | H | t-Bu |
| 33 | 2-F | 3-F | t-Bu |
| 34 | 2-tBu | 5-tBu | t-Bu |
| 35 | 3-CF$_3$ | H | t-Bu |
| 36 | 3-Cl | H | di-F |
| 37 | 3-Br | H | di-F |
| 38 | 2-F | 3-F | di-F |
| 39 | 2-tBu | 5-tBu | di-F |
| 40 | 3-CF$_3$ | H | tri-F |
| 41 | 3-Cl | H | tri-F |
| 42 | 3-Br | H | tri-F |
| 43 | 2-F | 3-F | Ph |
| 44 | 2-tBu | 5-tBu | Ph |
| 45 | 3-CF$_3$ | H | Ph |

TABLE 2

R^A = NH

| 化合物 (II-a) No | R2 | R3 | (R4) q |
|---|---|---|---|
| 46 | 3-Cl | H | F |
| 47 | 3-Br | H | F |
| 48 | 2-F | 3-F | F |
| 49 | 2-tBu | 5-tBu | F |
| 50 | 3-CF$_3$ | H | F |
| 51 | 3-Cl | H | Cl |
| 52 | 3-Br | H | Cl |
| 53 | 2-F | 3-F | Cl |
| 54 | 2-tBu | 5-tBu | Cl |
| 55 | 3-CF$_3$ | H | Cl |
| 56 | 3-Cl | H | Br |
| 57 | 3-Br | H | Br |
| 58 | 2-F | 3-F | Br |
| 59 | 2-tBu | 5-tBu | Br |
| 60 | 3-CF$_3$ | H | Br |
| 61 | 3-Cl | H | OCF$_3$ |
| 62 | 3-Br | H | OCF$_3$ |
| 63 | 2-F | 3-F | OCF$_3$ |
| 64 | 2-tBu | 5-tBu | OCF$_3$ |
| 65 | 3-CF$_3$ | H | OCF$_3$ |
| 66 | 3-Cl | H | OMe |
| 67 | 3-Br | H | OMe |
| 68 | 2-F | 3-F | OMe |
| 69 | 2-tBu | 5-tBu | OMe |
| 70 | 3-CF$_3$ | H | OMe |
| 71 | 3-Cl | H | Me |
| 72 | 3-Br | H | Me |
| 73 | 2-F | 3-F | Me |
| 74 | 2-tBu | 5-tBu | Me |
| 75 | 3-CF$_3$ | H | Me |
| 76 | 3-Cl | H | t-Bu |
| 77 | 3-Br | H | t-Bu |
| 78 | 2-F | 3-F | t-Bu |
| 79 | 2-tBu | 5-tBu | t-Bu |
| 80 | 3-CF$_3$ | H | t-Bu |
| 81 | 3-Cl | H | di-F |
| 82 | 3-Br | H | di-F |
| 83 | 2-F | 3-F | di-F |
| 84 | 2-tBu | 5-tBu | di-F |
| 85 | 3-CF$_3$ | H | tri-F |
| 86 | 3-Cl | H | tri-F |
| 87 | 3-Br | H | tri-F |
| 88 | 2-F | 3-F | Ph |
| 89 | 2-tBu | 5-tBu | Ph |
| 90 | 3-CF$_3$ | H | Ph |

TABLE 3

R^A = S

| 化合物 (II-a) No | R2 | R3 | (R4) q |
|---|---|---|---|
| 91 | 3-Cl | H | F |
| 92 | 3-Br | H | F |
| 93 | 2-F | 3-F | F |
| 94 | 2-tBu | 5-tBu | F |
| 95 | 3-CF$_3$ | H | F |
| 96 | 3-Cl | H | Cl |
| 97 | 3-Br | H | Cl |
| 98 | 2-F | 3-F | Cl |
| 99 | 2-tBu | 5-tBu | Cl |
| 100 | 3-CF$_3$ | H | Cl |
| 101 | 3-Cl | H | Br |
| 102 | 3-Br | H | Br |
| 103 | 2-F | 3-F | Br |
| 104 | 2-tBu | 5-tBu | Br |
| 105 | 3-CF$_3$ | H | Br |
| 106 | 3-Cl | H | OCF$_3$ |
| 107 | 3-Br | H | OCF$_3$ |
| 108 | 2-F | 3-F | OCF$_3$ |
| 109 | 2-tBu | 5-tBu | OCF$_3$ |
| 110 | 3-CF$_3$ | H | OCF$_3$ |
| 111 | 3-Cl | H | OMe |
| 112 | 3-Br | H | OMe |
| 113 | 2-F | 3-F | OMe |
| 114 | 2-tBu | 5-tBu | OMe |
| 115 | 3-CF$_3$ | H | OMe |
| 116 | 3-Cl | H | Me |
| 117 | 3-Br | H | Me |
| 118 | 2-F | 3-F | Me |
| 119 | 2-tBu | 5-tBu | Me |
| 120 | 3-CF$_3$ | H | Me |
| 121 | 3-Cl | H | t-Bu |
| 122 | 3-Br | H | t-Bu |
| 123 | 2-F | 3-F | t-Bu |
| 124 | 2-tBu | 5-tBu | t-Bu |
| 125 | 3-CF$_3$ | H | t-Bu |
| 126 | 3-Cl | H | di-F |
| 127 | 3-Br | H | di-F |

TABLE 3-continued

$R^A = S$

| 化合物 (II-a) No | R2 | R3 | (R4) q |
|---|---|---|---|
| 128 | 2-F | 3-F | di-F |
| 129 | 2-tBu | 5-tBu | di-F |
| 130 | 3-CF$_3$ | H | tri-F |
| 131 | 3-Cl | H | tri-F |
| 132 | 3-Br | H | tri-F |
| 133 | 2-F | 3-F | Ph |
| 134 | 2-tBu | 5-tBu | Ph |
| 135 | 3-CF$_3$ | H | Ph |

TABLE 4

$R^A = SO$

| 化合物 (II-a) No | R2 | R3 | (R4) q |
|---|---|---|---|
| 136 | 3-Cl | H | F |
| 137 | 3-Br | H | F |
| 138 | 2-F | 3-F | F |
| 139 | 2-tBu | 5-tBu | F |
| 140 | 3-CF$_3$ | H | F |
| 141 | 3-Cl | H | Cl |
| 142 | 3-Br | H | Cl |
| 143 | 2-F | 3-F | Cl |
| 144 | 2-tBu | 5-tBu | Cl |
| 145 | 3-CF$_3$ | H | Cl |
| 146 | 3-Cl | H | Br |
| 147 | 3-Br | H | Br |
| 148 | 2-F | 3-F | Br |
| 149 | 2-tBu | 5-tBu | Br |
| 150 | 3-CF$_3$ | H | Br |
| 151 | 3-Cl | H | OCF$_3$ |
| 152 | 3-Br | H | OCF$_3$ |
| 153 | 2-F | 3-F | OCF$_3$ |
| 154 | 2-tBu | 5-tBu | OCF$_3$ |
| 155 | 3-CF$_3$ | H | OCF$_3$ |
| 156 | 3-Cl | H | OMe |
| 157 | 3-Br | H | OMe |
| 158 | 2-F | 3-F | OMe |
| 159 | 2-tBu | 5-tBu | OMe |
| 160 | 3-CF$_3$ | H | OMe |
| 161 | 3-Cl | H | Me |
| 162 | 3-Br | H | Me |
| 163 | 2-F | 3-F | Me |
| 164 | 2-tBu | 5-tBu | Me |
| 165 | 3-CF$_3$ | H | Me |
| 166 | 3-Cl | H | t-Bu |
| 167 | 3-Br | H | t-Bu |
| 168 | 2-F | 3-F | t-Bu |
| 169 | 2-tBu | 5-tBu | t-Bu |
| 170 | 3-CF$_3$ | H | t-Bu |
| 171 | 3-Cl | H | di-F |
| 172 | 3-Br | H | di-F |
| 173 | 2-F | 3-F | di-F |
| 174 | 2-tBu | 5-tBu | di-F |
| 175 | 3-CF$_3$ | H | tri-F |
| 176 | 3-Cl | H | tri-F |
| 177 | 3-Br | H | tri-F |
| 178 | 2-F | 3-F | Ph |
| 179 | 2-tBu | 5-tBu | Ph |
| 180 | 3-CF$_3$ | H | Ph |

TABLE 5

$R^A = SO_2$

| 化合物 (II-a) No | R2 | R3 | (R4) q |
|---|---|---|---|
| 181 | 3-Cl | H | F |
| 182 | 3-Br | H | F |
| 183 | 2-F | 3-F | F |

TABLE 5-continued

$R^A = SO_2$

| 化合物 (II-a) No | R2 | R3 | (R4) q |
|---|---|---|---|
| 184 | 2-tBu | 5-tBu | F |
| 185 | 3-CF$_3$ | H | F |
| 186 | 3-Cl | H | Cl |
| 187 | 3-Br | H | Cl |
| 188 | 2-F | 3-F | Cl |
| 189 | 2-tBu | 5-tBu | Cl |
| 190 | 3-CF$_3$ | H | Cl |
| 191 | 3-Cl | H | Br |
| 192 | 3-Br | H | Br |
| 193 | 2-F | 3-F | Br |
| 194 | 2-tBu | 5-tBu | Br |
| 195 | 3-CF$_3$ | H | Br |
| 196 | 3-Cl | H | OCF$_3$ |
| 197 | 3-Br | H | OCF$_3$ |
| 198 | 2-F | 3-F | OCF$_3$ |
| 199 | 2-tBu | 5-tBu | OCF$_3$ |
| 200 | 3-CF$_3$ | H | OCF$_3$ |
| 201 | 3-Cl | H | OMe |
| 202 | 3-Br | H | OMe |
| 203 | 2-F | 3-F | OMe |
| 204 | 2-tBu | 5-tBu | OMe |
| 205 | 3-CF$_3$ | H | OMe |
| 206 | 3-Cl | H | Me |
| 207 | 3-Br | H | Me |
| 208 | 2-F | 3-F | Me |
| 209 | 2-tBu | 5-tBu | Me |
| 210 | 3-CF$_3$ | H | Me |
| 211 | 3-Cl | H | t-Bu |
| 212 | 3-Br | H | t-Bu |
| 213 | 2-F | 3-F | t-Bu |
| 214 | 2-tBu | 5-tBu | t-Bu |
| 215 | 3-CF$_3$ | H | t-Bu |
| 216 | 3-Cl | H | di-F |
| 217 | 3-Br | H | di-F |
| 218 | 2-F | 3-F | di-F |
| 219 | 2-tBu | 5-tBu | di-F |
| 220 | 3-CF$_3$ | H | tri-F |
| 221 | 3-Cl | H | tri-F |
| 222 | 3-Br | H | tri-F |
| 223 | 2-F | 3-F | Ph |
| 224 | 2-tBu | 5-tBu | Ph |
| 225 | 3-CF$_3$ | H | Ph |

EXAMPLES 7–16

As compound (I), following compounds and/or the salt were prepared.

Ex 7

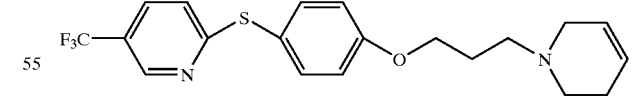

Ex 8

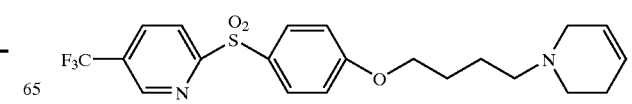

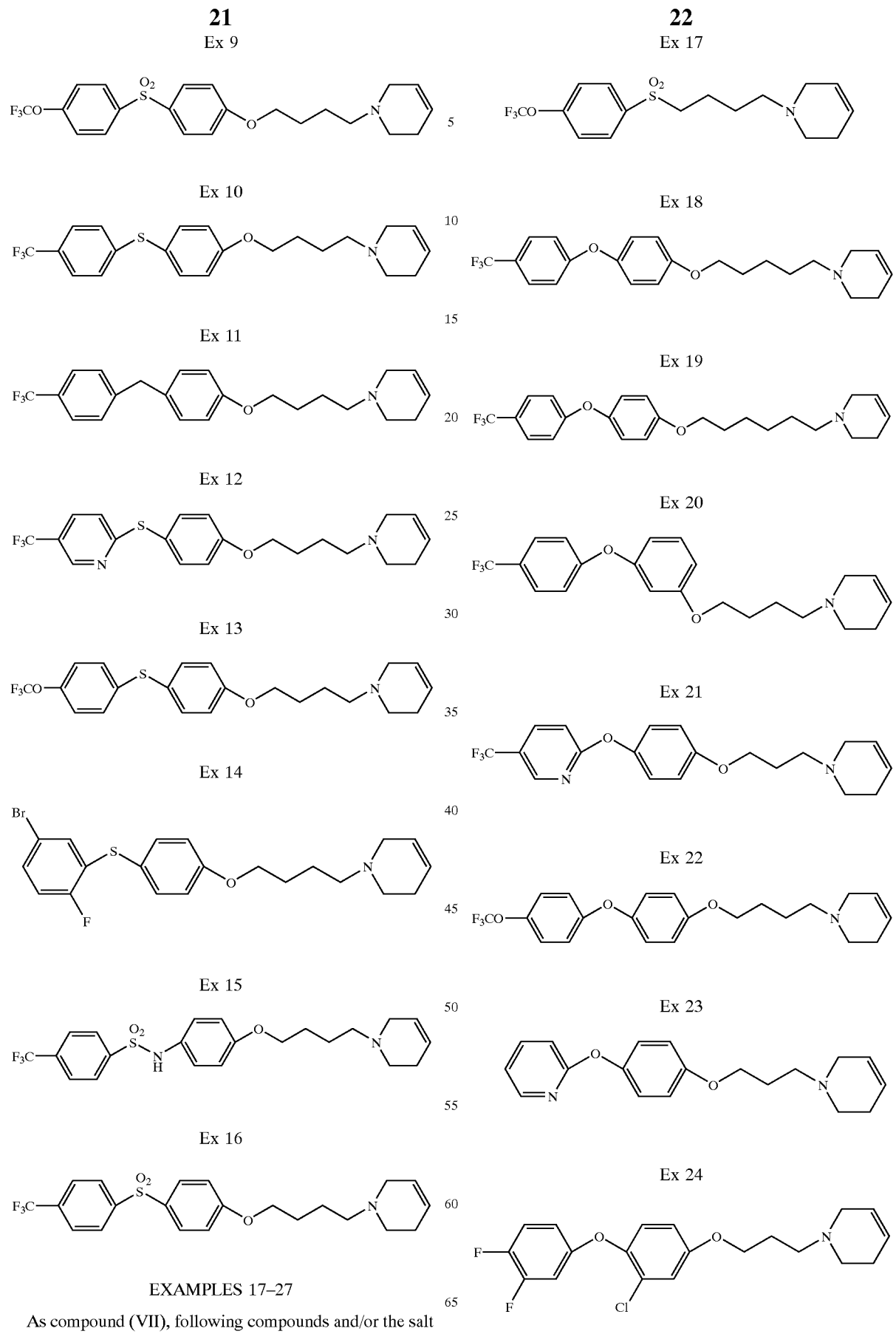
EXAMPLES 17–27
As compound (VII), following compounds and/or the salt were prepared.

Ex 25

[Structure: F, F-substituted phenyl-O-phenyl(Cl)-O-(CH2)4-N-tetrahydropyridine]

Ex 26

[Structure: F3C-pyridyl-O-phenyl-O-(CH2)4-N-tetrahydropyridine]

Ex 27

[Structure: F3CO-phenyl-O-phenyl-O-(CH2)3-N-tetrahydropyridine]

Physical properties of compounds described for Examples 7–27 were shown below.

Ex 7

NMR (CDCl$_3$)δ ppm (300 MHz) (Free) 2.063(2H, t, J=8 Hz), 2.15~2.25(2H, m), 2.58~2.66(2H, m), 4.090(2H, t, J=6 Hz), 5.65~5.80(2H, m), 6.853(2H, d, J=9 Hz), 7.000(2H, d, J=9 Hz), 7.514(2H, d, J=9 Hz), 7.607(1H, dd, J=9 Hz, 3 Hz), 8.640(1H, m)

Anal. (%): C$_{20}$H$_{21}$F$_3$N$_2$OS.HCl

Calcd.: C=55.75, H=5.15, N=6.50, Cl=8.23, F=13.23, S=7.44.

Found: C=55.55, H=4.96, N=6.38, Cl=8.52, F=13.23, S=7.44.

Ex 8

NMR (CDCl$_3$)δ ppm (300 MHz) (Free) 1.64~1.83(4H, m), 1.842(2H, quint, J=7 Hz), 2.14~2.23(2H, m), 2.475(2H, t, J=8 Hz), 2.569(2H, t, J=6 Hz), 2.95~3.01(2H, m), 4.047 (2H, t, J=6 Hz), 5.63~5.80(2H, m), 7.001(2H, d, J=9 Hz), 7.984(2H, d, J=9 Hz), 8.157(1H, m), 8.308(1H, d, J=8 Hz), 8.900(1H, m)

Anal. (%): C$_{21}$H$_{23}$F$_3$N$_2$O$_3$S.HCl

Calcd.: C=52.88, H=5.07, N=5.87, Cl=7.43, F=11.95, S=6.72,

Found : C=52.49, H=5.07, N=5.76, Cl=7.46, F=11.78, S=6.70,

Ex 9

NMR (CDCl$_3$)δ ppm (300 MHz) (Free) 1.68~1.77(2H, m), 1.79~1.88(2H, m), 2.16~2.24(2H, m), 2.52(2H, t, J=7.5 Hz), 2.62(2H, t, J=6.0 Hz), 3.01~3.05(2H, m), 4.03(2H, t, J=6.0 Hz), 5.66(1H, m), 5.77 (1H, m), 6.97(2H, d, J=9.0 Hz), 7.31(2H, d, J=9.0 Hz), 7.86(2H, d, J=9.0 Hz), 7.96(2H, d, J=9.0 Hz).

Anal. (%): C$_{22}$H$_{24}$F$_3$NO$_4$S.C$_2$H$_2$O$_4$.0.2 H$_2$O.0.2 2-PrOH

Calcd.: C=52.65,H=5.03,F=10.16,N=2.50,S=5.71.

Found: C=52.71,H=4.75,F=9.89,N=2.61,S=5.81.

Ex 10

NMR (CDCl$_3$)δ ppm (300 MHz) (Free) 1.733(2H, quint, J=6.9 Hz), 1.850(2H, quint, J=7.5 Hz), 2.15~2.25(2H, m), 2.484(2H, t, J=7.5 Hz), 2.572(2H, t, J=6 Hz), 2.95~3.00(2H, m), 4.020(2H, t, J=6.3 Hz), 5.62~5.80(2H, m), 6.942(2H, d, J=8.7 Hz), 7.129(2H, d, J=7.8 Hz), 7.429(2H, d, J=7.8 Hz), 7.449(2H, d, J=8.7 Hz), Anal. (%): C$_{22}$H$_{24}$F$_3$NOS.HCl Calcd.: C=59.52, H=5.68, N=3.15, Cl=7.99, F=12.84, S=7.22.

Found: C=59.30, H=5.43, N=3.21, Cl=7.96, F=12.85, S=7.03.

Ex 11

NMR (CDCl$_3$)δ ppm (300 MHz) (Free) 1.76~1.86(4H, m), 2.14~2.22(2H, m), 2.460(2H, t, J=7.5 Hz), 2.555(2H, t, J=5.7 Hz), 2.94~3.00(2H, m), 3.955(2H, t, J=6.3 Hz), 3.960 (2H, S) 5.62~5.78(2H, m), 6.828(2H, d, J=8.4 Hz), 7.068 (2H, d, J=8.4 Hz), 7.271(2H, d, J=8.4 Hz), 7.521(2H, d, J=8.4 Hz), Anal. (%): C$_{23}$H$_{26}$F$_3$NO$_2$.HCl Calcd.: C=64.86, H=6.39, N=3.29, Cl=8.32, F=13.38, Found: C=64.76, H=6.39, N=3.35, Cl=8.28, F=13.26,

Ex 12

NMR (CDCl$_3$)δ ppm (300 MHz) (Free) 1.68~1.85(2H, m), 1.862(2H, quint, J=7 Hz), 2.15~2.24(2H, m), 2.490(2H, t, J=7.0 Hz), 2.576(2H, t, J=6 Hz), 2.96~3.02(2H, m), 4.038(2H, t, J=6 Hz), 5.64~5.80(2H, m), 6.854(1H, d, J=9 Hz), 6.983(2H, d, J=9 Hz), 7.512(2H, d, J=9 Hz), 7.605(1H, dd, J=9 Hz, 2 Hz), 8.635(1H, m)

Anal. (%): C$_{21}$H$_{23}$F$_3$N$_2$OS.HCl.0.1 H$_2$O

Calcd.: C=56.69, H=5.44, N=6.30, Cl=7.97, F=12.81.

Found: C=56.46, H=5.46, N=6.27, Cl=7.94, F=12.76.

Ex 13

NMR (CDCl$_3$)δ ppm (300 MHz) (Free) 1.84~1.88(4H, m), 2.28~2.36(2H, m), 2.63~2.72(2H, m), 2.78(2H, t, J=5.7 Hz), 3.16~3.22(2H, m), 4.01(2H, t, J=5.7 Hz), 5.68(1H, m), 5.83(1H, m), 6.90(2H, d, J=9.0 Hz), 7.07(2H, d, J=9.0 Hz), 7.14(2H, d, J=9.0 Hz), 7.41(2H, d, J=9.0 Hz).

Anal. (%): C$_{22}$H$_{24}$F$_3$NO$_2$S.C$_2$H$_2$O$_4$.0.1 H$_2$O

Calcd.: C=55.94, H=5.12, N=5.76, F=11.06, S=6.24.

Found: C=55.96, H=5.04, N=2.81, F=10.79, S=6.13.

Ex 14

NMR (CDCl$_3$)δ ppm (300 MHz) (Free) 1.67~1.91(4H, m), 2.15~2.24(2H, m), 2.50(2H, t, J=7.4 Hz), 2.58(2H, t, J=5.8 Hz), 2.97~3.02(2H, m), 4.02(2H, t, J=6.2 Hz), 5.63~5.71(1H, m), 5.72~5.81(1H, m), 6.87~6.97(4H, m), 7.21(1H, ddd, J=8.7, 4.5, 2.5 Hz), 7.43(2H, d, J=8.8 Hz)

Anal.: C$_{21}$H$_{23}$F$_3$NBrOS.HCl

Calcd.: C=53.34,H=5.12, N=2.96 Br=16.90, Cl=7.50, F=4.02, S=6.78.

Found: C=53.16,H=5.12, N=3.11 Br=16.83, Cl=7.22, F=3.90, S=6.62.

Ex 15

NMR (CDCl$_3$)δ ppm (300 MHz) (Free) 1.60~1.86(4H, m), 2.12~2.24(2H, m), 2.463(2H, t, J=6.9 Hz), 2.569(2H, t, J=5.7 Hz), 2.94~3.02(2H, m), 3.909(2H, t, J=6.3 Hz), 4.20~4.70(1H, m), 5.60~5.80(2H, m), 6.755(2H, d, J=8.7 Hz), 6.959(2H, d, J=8.7 Hz), 7.688(2H, d, J=8.7 Hz), 7.817(2H, d, J=8.7 Hz), Anal. (%): C$_{22}$H$_{25}$F$_3$N$_2$O$_3$S.C$_2$H$_2$O$_4$ Calcd.: C=52.94, H=5.00, N=5.14, F=10.47, S=5.89.

Found : C=52.71, H=4.78, N=5.09, F=10.69, S=6.05.

Ex 16

NMR (CDCl$_3$)δ ppm (300 MHz) (Free) 1.86~1.68(6H, m). 2.19(2H, m), 2.48(2H, t, J=7.2), 2.58(2H, t, J=5.7), 4.03(2H, t, J=6.0), 5.68~5.63(1H, m), 5.78~5.73(1H, m), 6.93(2H, d, J=9.3), 7.75 (2H, d, J=9.0), 7.86(2H, d, J=9.3), 8.04(2H, d, J=9.0), Anal. (%): $C_{22}H_{24}F_3NO_3S.HCl.1.1\ H_2O$ Calcd.: C=53.30,H=5.53,N=2.83 Cl=7.15 F=11.50, S=6.47.

Found: C=53.19,H=5.10,N=2.94 Cl=6.25 F=11.64, S=6.48.

Ex 17

NMR (CDCl$_3$)δ ppm (300 MHz) (Free) 1.617(2H, quint, J=7.2 Hz), 1.773(2H, quint, J=7.8 Hz), 2.08~2.20(2H, m), 2.376(2H, t, J=7.5 Hz), 2.491(2H, t, J=5.4 Hz), 2.87~2.94 (2H, m), 3.156(2H, t, J=7.8 Hz), 5.58~5.78(2H, m), 7.398 (2H, d, J=9 Hz), 7.969(2H, d, J=9 Hz), Anal. (%): $C_{16}H_{20}F_3NO_3S.HCl$ Calcd.: C=48.06, H=5.29, N=3.50, Cl=8.87, F=14.25, S=8.02.

Found: C=47.91, H=5.15, N=3.41, Cl=8.73, F=14.25, S=7.94.

Ex 18

NMR (CDCl$_3$)δ ppm (300 MHz)(Free) 1.45~1.90(6H, m), 2.15~2.25(2H, m), 2.435(2H, t, J=7.8 Hz), 2.559(2H, t, J=5.7 Hz), 2.94~3.00(2H, m), 3.961(2H, t, J=6.6 Hz), 5.64~5.80(2H, m), 6.87~7.02(2H, m) 7.533(2H, d, J=8.4 Hz)

Anal. (%): $C_{23}H_{26}F_3NO_2.HCl.0.25\ H_2O$

Calcd.: C=61.88, H=6.21, N=3.14, Cl=7.94, F=12.77.

Found: C=61.97, H=6.06, N=3.27, Cl=8.04, F=12.73.

Ex 19

NMR (CDCl$_3$)δ ppm (300 MHz) (Free) 1.35~1.65(6H, m), 1.805(2H, quint, quint, J=6.6 Hz), 2.14~2.24(2H, m), 2.411(2H, t, J=7.5 Hz), 2.551(2H, t, J=6 Hz), 2.94~3.02(2H, m), 3.952(2H, t, J=6 Hz), 5.62~5.80(2H, m), 6.88~7.04(2H, m), 7.531(2H, d, J=8.4 Hz)

Anal. (%): $C_{24}H_{28}F_3NO_2.HCl$

Calcd.: C=63.22, H=6.41, N=3.07, Cl=7.78, F=12.50.

Found: C=63.04, H=6.43, N=3.14, Cl=7.81, F=12.59.

Ex 20

NMR (CDCl$_3$)δ ppm (300 MHz) (Free) 1.65~1.90(4H, m), 2.14~2.24(2H, m), 2.460(2H, t, J=7.2 Hz), 2.556(2H, t, J=5.7 Hz), 2.94~3.00(2H, m), 3.959(2H, t, J=6.3 Hz), 5.60~5.80(2H, m), 6.57~6.75(3H, m), 7.055(2H, d, J=8.7 Hz), 7.259(1H, d, J=16.2 Hz), 7.570(2H, d, J=9.0 Hz), Anal. (%): $C_{22}H_{24}F_3NO_2.HCl$ Calcd.: C=61.75, H=5.89, N=3.27, Cl=8.29, F=13.32.

Found: C=61.86, H=5.80, N=3.34, Cl=8.23, F=13.34.

Ex 21

NMR (CDCl$_3$)δ ppm (300 MHz) (Free) 2.030(2H, quint, J=6 Hz), 2.16~2.24(2H, m), 2.56~2.64(4H, m), 2.98~3.03 (2H, m), 4.040(2H, t, J=6 Hz), 5.64~5.81(2H, m), 6.91~7.19 (5H, m), 7.869(1H, dd, J=9 Hz, 3 Hz), 8.430(1H, m)

Anal. (%): $C_{20}H_{21}F_3N_2O_2S.HCl.0.1\ Et_2O$

Calcd.: C=62.74,H=5.79,F=14.89,N=7.32,Cl=9.26.

Found: C=62.78,H=5.94,F=14.60,N=7.18,Cl=9.08.

Ex 22

NMR (CDCl$_3$)δ ppm (300 MHz) (Free) 1.68~1.90(4H, m), 2.16~2.22(2H, m), 2.475(2H, t, J=7.2 Hz), 2.567(2H, t, J=5.7 Hz), 3.972(2H, t, J=6.0 Hz), 5.64~5.80(2H, m), 6.86~7.00(6H, m), 7.134(2H, d, J=9.0 Hz), Anal. (%): $C_{22}H_{24}F_3NO_3.HCl$ Calcd.: C=59.53, H=5.68, N=3.16, Cl=7.99, F=12.84.

Found: C=59.41, H=5.63, N=3.26, Cl=8.10, F=12.81.

Ex 23

NMR (CDCl$_3$)δ ppm (300 MHz) (Free) 2.024(2H, quint, J=7.5 Hz), 2.16~2.24(2H, m), 2.56~2.64(4H, m), 2.98~3.03 (2H, m), 4.027(2H, t, J=6.0 Hz), 5.64~5.80(2H, m), 6.83~7.08(6H, m), 7.651 (1H, m), 8.18(1H, m)

Anal. (%): $C_{19}H_{22}N_2O_2.C_2H_2O_4$

Calcd.: C=62.99,H=6.04,N=7.00.

Found: C=62.91,H=6.01,N=6.97.

Ex 24

NMR (CDCl$_3$)δ ppm (300 MHz) (Free) 2.023(2H, quint, J=6.6 Hz), 2.15~2.25(2H,m), 2.55~2.65(2H,m), 2.96~3.06 (2H, m), 4.026(2H, t, J=6 Hz), 5.64~5.82(2H, m), 6.55~7.10 (2H, m), Anal. (%): $C_{20}H_{20}ClF_2NO_2.HCl$ Calcd.: C=57.70, H=5.08, N=3.36, Cl=17.03, F=9.13.

Found: C=57.62, H=5.12, N=3.44, Cl=16.95, F=8.95.

Ex 25

NMR (CDCl$_3$)δ ppm (300 MHz) (Free) 1.65~1.90(4H, m), 2.15~2.24(2H, m), 2.485(2H, t, J=7.5 Hz), 2.581(2H, t, J=6.0 Hz), 2.95~3.03(2H, m), 3.972(2H, t, J=6.3 Hz), 5.62~5.80(2H, m), 6.55~7.10(6H, m), Anal. (%): $C_{21}H_{22}ClF_2NO_2.HCl$ Calcd.: C=58.61, H=5.39, N=3.25, Cl=16.48, F=8.83.

Found: C=58.59, H=5.37, N=3.28, Cl=16.26, F=8.40.

Ex 26

NMR (CDCl$_3$)δ ppm (300 MHz) (Free) 1.63–1.84(4H, m), 1.833(2H, quint, J=7.5 Hz), 2.15~2.24(2H, m), 2.480 (2H, t, J=7.5 Hz), 2.574(2H, t, J=6 Hz), 2.95~3.02(2H, m), 3.991(2H, t, J=6 Hz), 5.64~5.80(2H, m), 6.90~7.09(5H, m), 7.869(1H, dd, J=9 Hz, 3 Hz), 8.440(1H, m)

Anal. (%): $C_{21}H_{23}F_3N_2O_2.HCl$

Calcd.: C=58.81, H=5.64, N=6.53, Cl=8.27, F=13.29.

Found: C=58.70, H=5.66, N=6.49, Cl=8.32 , F=13.17.

Ex 27

NMR (CDCl$_3$)δ ppm (300 MHz) (Free) 1.95~2.25(4H, m), 2.55~2.65(4H, m), 2.97~3.04(4H, m), 4.020(2H, t, J=6.6 Hz), 5.64~5.80 (2H, m), 6.84~7.00(6H, m), 7.135(2H, d, J=9.0 Hz), Anal. (%): $C_{21}H_{22}F_3NO_3.HCl$ Calcd.: C=58.68, H=5.39, N=3.26, Cl=8.25, F=13.26.

Found: C=58.49, H=5.16, N=3.35, Cl=8.22, F=13.28.

EXPERIMENTAL EXAMPLE 1

After 80 mg/kg of the present compound was administered subcutaneously for 7 days to 7–8 week aged male KK-Ay mouse (n=5~7, CLEA JAPAN, INC), the amount of food intake from seventh day to eighth day, and body weight of eighth day were measured. For a control group, physiological saline was used. After the body weight was measured, the blood was collected from abdominal aorta by a syringe containing 50 U heparin and centrifuged 12,000×g for five min. Glucose in blood was measured by New Blood•Sugar•Test (Boehringer Ingelheim) and insulin was measured by Insulin-EIA Test (GLAOZYME). Measurement results are shown below by relative values to 100, which is a value of the control group.

TABLE 6

| Ex (Compound No) | Dose (80 mg/kg)(S.C) | | |
|---|---|---|---|
| | Body weight | Glucose | Insulin |
| 3 (23) | 82** | 25** | 22** |
| 5 (25) | 73** | 23** | 8** |

*P < 0.05,
**P < 0.01 vs. Vehicle

The present compound has the decreasing effect of body weight, remarkable decreases of Insulin and Glucose concentrations in blood in an administrated group in comparisom with reference group. Futhermore, prefered compound showed well oral absorbability, high concentration in blood and weak inhibitory effect against metabolic enzymes and did not show any side effects on central nervous systems, digestive organs and so on.

FORMULATION EXAMPLE 1

The present compound, crystalline cellulose, magnesium stearate and the like, each proper amount was mixed and the mixture was tabletted to give tablets.

FORMULATION EXAMPLE 2

After the present compound, lactose, magnesium stearate and the like, each proper amount was mixed and the mixture was extruded to give granules.

FORMULATION EXAMPLE 3

The granule of Formulation Example 2 was capsulated to give capsules.

INDUSTRIAL APPLICABILITY

The present compound is for use as an anti obestic agent, a preventive and therapeutic agent for diabetes and the like.

What is claimed is:

1. A composition for use as an antiobestic agent, containing a compound of the formula (I):

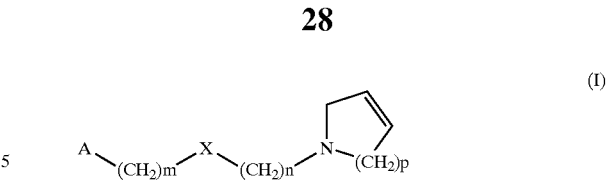

wherein A is aryl or heteroaryl, each substituted with one or more substituent(s), (wherein the substituent includes at least a group of —$R^A$—$R^B$ ($R^A$ is S, SO, $SO_2$, $NR^C$, $NR^CSO_2$ ($R^C$ is hydrogen or lower alkyl) or lower alkylene; $R^B$ is optionally substituted aryl);

X is O, S, NR (R is hydrogen or lower alkyl), or a bond;

m is an integer of 0 to 4;

n is an integer of 1 to 6;

p is an integer of 1 to 3, pharmaceutically acceptable salt, prodrug or solvate thereof.

2. The composition for use as an antiobestic agent described in claim 1 wherein X is O.

3. The composition for use as an antiobestic agent described in claim 1 wherein m is 0.

4. The composition for use as an antiobestic agent described in claim 1 wherein n is 2 to 4.

5. The composition for use as an antiobestic agent described in claim 1 wherein p is 2.

6. The composition for use as an antiobestic agent described in above 1 wherein X is O; m is 0; n is 2 to 4; and p is 2.

7. The composition for use as an antiobestic agent described in claim 1 wherein A is a phenyl group substituted with —$R^A$—$R^B$ ($R^A$ and $R^B$ are the same meaning as described above).

8. The composition for use as an antiobestic agent described in claim 7 wherein $R^B$ is phenyl or pyridinyl, each substituted with same or different, one to three group(s) selected from the group consisting of halogen, hydroxy, lower alkyl, halogenated lower alkyl, lower alkoxy, halogenated lower alkoxy and phenyl.

9. The composition for use as an antiobestic agent described in claim 1 wherein X is O; m is 0; n is 2 to 4; p is 2; and A is phenyl substituted with —$R^A$—$R^B$ ($R^A$ is the same meaning as described above; $R^B$ is substituted phenyl or substituted pyridinyl).

10. The composition for use as an antiobestic agent described in claim 9 wherein $R^B$ is phenyl or pyridinyl, each substituted with halogen, halogenated lower alkyl or halogenated lower alkoxy.

11. A composition for use as a preventive or therapeutic agent for diabetes containing a compound described in any one of claims 1 to 10 and a pharmaceutically acceptable additive.

* * * * *